United States Patent [19]
McNelis et al.

[11] Patent Number: 5,788,910
[45] Date of Patent: Aug. 4, 1998

[54] POST FORMED CURVED TAMPON ASSEMBLY

[75] Inventors: Thomas C. McNelis; Robert C. Norquest, both of Dover, Del.

[73] Assignee: Playtex Products, Inc., Westport, Conn.

[21] Appl. No.: 899,491

[22] Filed: Jul. 19, 1997

Related U.S. Application Data

[63] Continuation of Ser. No. 500,159, Jul. 11, 1995, abandoned.

[51] Int. Cl.[6] .................................................. B29C 43/02
[52] U.S. Cl. .................................. 264/296; 264/322
[58] Field of Search ............................... 264/294, 296, 264/322; 604/14, 15, 904

[56] References Cited

U.S. PATENT DOCUMENTS

| | | | |
|---|---|---|---|
| 3,765,417 | 10/1973 | Crockford | 604/15 |
| 3,884,612 | 5/1975 | Parmann | 425/392 |
| 4,368,023 | 1/1983 | Hannah et al. | 425/392 |
| 4,786,456 | 11/1988 | Witte | 425/392 |
| 5,066,212 | 11/1991 | Moran, Jr. | 425/392 |
| 5,084,038 | 1/1992 | Sheldon et al. | 604/904 |
| 5,151,241 | 9/1992 | Maier et al. | 264/322 |
| 5,153,971 | 10/1992 | Van Iten | 28/118 |
| 5,158,535 | 10/1992 | Paul et al. | 604/15 |
| 5,267,953 | 12/1993 | Paul et al. | 604/15 |
| 5,350,371 | 9/1994 | Van Iten | 604/398 |
| 5,395,308 | 3/1995 | Fox et al. | 604/15 |
| 5,407,613 | 4/1995 | Schulte | 264/322 |
| 5,437,628 | 8/1995 | Fox et al. | 604/14 |

*Primary Examiner*—Jan H. Silbaugh
*Assistant Examiner*—Mark Eashoo
*Attorney, Agent, or Firm*—Ohlandt, Greeley, Ruggiero & Perle

[57] ABSTRACT

There is provided a method for post forming an assembled tampon assembly into a curved tampon assembly. Before employing this method, the tampon assembly is completely formed using existing manufacturing methods into a typical straight axial oriented tampon assembly. The tampon assembly is then heated to permit flexing and reorientation of the axis of one or more portions of the tampon assembly. Next, the heated tampon assembly is positioned in a mold cavity of a cold forming mold. The inner surface of one or more portions of the mold cavity has a desired arcuate shape or axial orientation in order to obtain a desired predetermined radius of curvature. Thereafter, the tampon assembly is held in the mold until the various components of the tampon assembly cool down. Finally, the cooled tampon assembly is removed from the mold and is ready to be packaged for distribution.

25 Claims, 3 Drawing Sheets

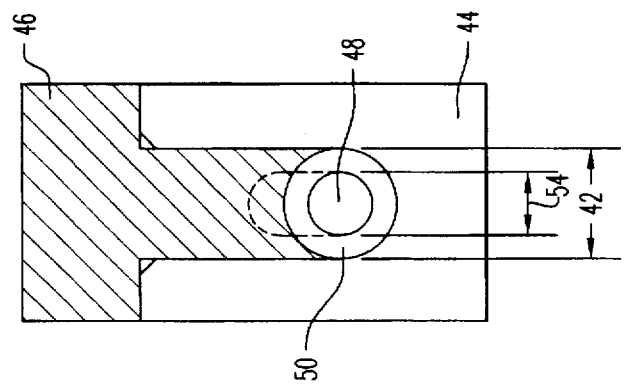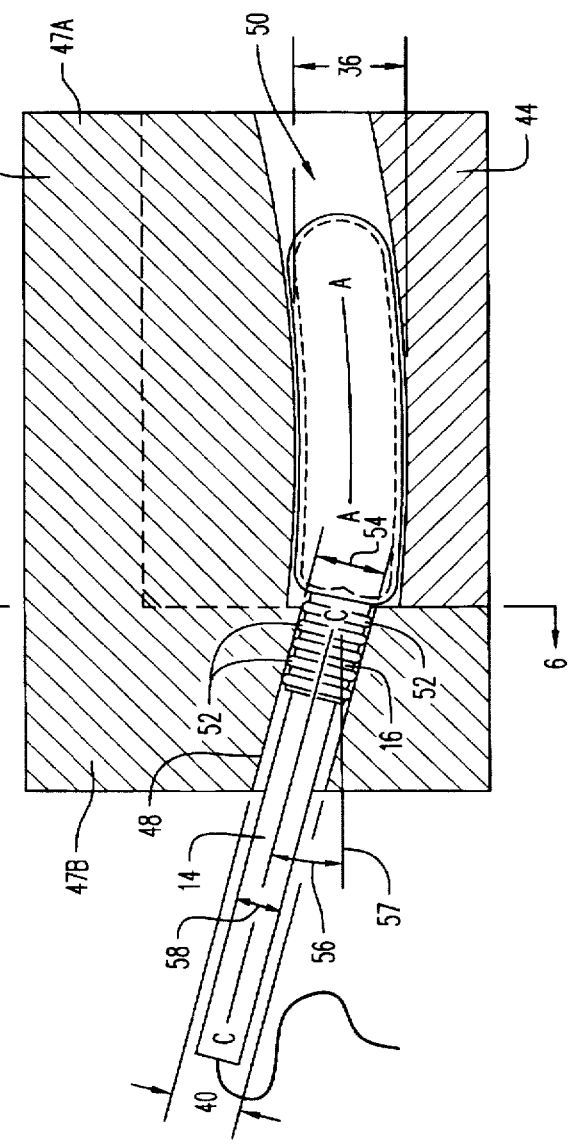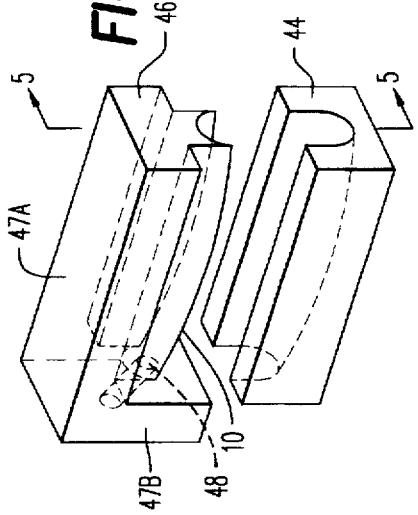

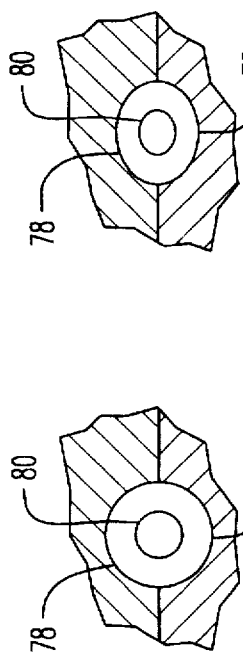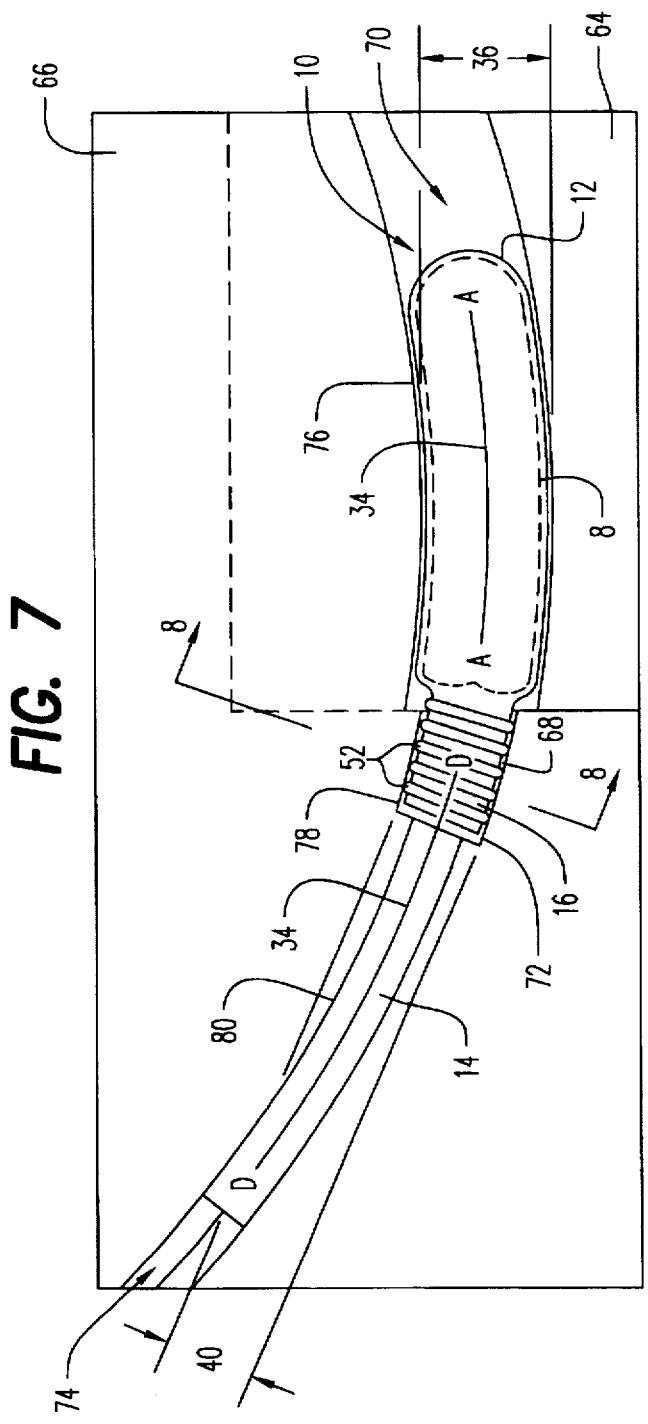

5,788,910

1

POST FORMED CURVED TAMPON ASSEMBLY

This is a continuation of application Ser. No. 08/500,159, filed Jul. 11, 1995, now abandoned.

BACKGROUND OF THE INVENTION

I. Field of the Invention

The present invention relates generally to tampon assemblies including an applicator and a pledget for vaginal insertion of tampon pledgets. More particularly, the present invention relates to a method for post forming a plastic-type tampon assembly into a curved axial orientation but after the initial formation and assembly of the tampon assembly components into a normal, straight-formed tampon assembly.

II. Description of the Prior Art

Generally, methods for forming curved-type tampons pledgets are known. For example, U.S. Pat. No. 5,153,971 to T. P. Van Iten, which issued on Oct. 13, 1992, and related U.S. Pat. No. 5,350,371 to also T. P. Van Iten, which issued on Sep. 27, 1994, provide a method for forming a curved tampon pledget. The pledget is constructed having two different zones of fiber density and inserted into a mold cavity having two open ends. Then, the pledget is compressed at both open ends and, optionally, heated about its periphery within the mold cavity. Next, the pledget exits the mold cavity having a straight form but quickly blossoms into a curved shaped pledget due to the differing expansion properties of its two zones of fiber density. Thereafter, the pledget may be positioned within a curved tampon applicator to complete assembly of the tampon assembly.

In addition to curved-type tampon pledgets, methods for forming curved plastic tampon applicators for inserting pledgets are also known. Such tampon applicators are typically manufactured using curved plastic components, such as a barrels and plungers, that are molded or extruded in a predetermined curved configuration and then assembled with the pledget to provide the finished curved tampon applicator product. For example, U.S. Pat. No. 5,158,535 to S. C. Paul, et al., which issued on Oct. 27, 1992, and U.S. Pat. No. 5,267,953 to also S. C. Paul, et al., which issued on Dec. 7, 1993 and is a divisional based on the U.S. Pat. No. 5,158,535, provide a method for forming a barrel and plunger of a curved tampon applicator by injection molding or extrusion. The straight barrel and plunger are individually heat set into an arcuate axial orientation. The barrel has a degree of axial curvature that is greater than that of its original shape. Then, the plunger is inserted into one end of the barrel and, thereafter, a tampon pledget is assembled within the other end of the barrel to complete the formation of the tampon assembly.

The above patents describe processes for forming curved components, such as the pledget, barrel and plunger, that are subsequently assembled together. Such assembly complicates production and is more difficult since manipulating, sorting and orienting such curved components requires special attention and expensive assembly machinery. In addition, the formation through the use of curved molds is more difficult than conventional straight counterparts.

Therefore, there is a need for a new and improved method for permitting tampon components to be manufactured as existing straight cylindrical components and assembled using pre-established high speed assembly methods while, subsequently, reforming or reorienting the complete tampon assembly into a curved configuration without further manufacturing or assembly of components.

2

SUMMARY OF THE INVENTION

Against the foregoing background, it is a primary object of the present invention to provide a method of post forming a conventional, axially straight, plastic-type tampon assembly into an axially curved tampon assembly.

It is another object of the present invention to provide such a method for post forming into a curved tampon assembly that is efficient and economical.

It is a further object of the present invention to provide such a method for post forming into a curved tampon assembly that permits existing high speed equipment to be used to manufacture and assemble the components of the tampon assembly thereby eliminating the need for curved cavity injection molds, plastic unscrambling and orienting equipment, and new or modified assembling machines for curved components.

To accomplish the foregoing objects and advantages, the present invention, in brief summary, comprises the following steps: heating a portion of the formed tampon assembly to a predetermined elevated temperature, to permit the portion to flex and thereby reorient the axis of the portion. The portion of the tampon assembly is then positioned in a mold cavity that has a longitudinal arcuate shape or bend having a desired, predetermined radius of curvature such that the positioning of the portion of the tampon assembly in the mold cavity causes the portion to initially adapt to the arcuate orientation of the mold cavity. Thereafter, the portion of the tampon assembly is held in the mold cavity until the tampon assembly cools to a predetermined reduced temperature. Lastly, the portion of the tampon assembly is removed from the mold cavity.

For another embodiment, the present invention comprises the following steps: heating a formed tampon assembly that includes a tampon pledget and a tampon applicator to a predetermined elevated temperature, to permit the tampon assembly to flex and thereby reorient the axis of the tampon assembly. The tampon assembly is then positioned in a mold cavity that has a longitudinal arcuate shape or bend having a desired, predetermined radius of curvature such that the positioning of the tampon assembly in the mold cavity causes the tampon assembly to initially adapt to the arcuate orientation of the mold cavity. Thereafter, the tampon assembly is held in the mold cavity until the tampon assembly cools to a predetermined reduced temperature. Lastly, the tampon assembly is removed from the mold cavity.

BRIEF DESCRIPTION OF THE DRAWINGS

The foregoing and still further the objects and advantages of the present invention will be more apparent from the following detailed explanation of the preferred embodiments of the invention in connection with the accompanying drawings:

FIG. 4 is a perspective view of a two-part mold and curved tampon assembly formed therein in accordance with a second preferred embodiment of the present invention;

FIG. 5 is a cut-away view taken along line 6—6 of FIG. 5 with the upper and lower mold of the two-part mold joined together; and FIG. 6 is a sectional view taken along line 6—6 of FIG. 5 but with the curved tampon assembly not shown;

FIG. 7 is a cut-away view of a third two-part mold and curved tampon assembly formed therein in accordance with a third preferred embodiment of the present invention;

FIG. 8 is a sectional view of the fingergrip of the curved tampon assembly taken along line 8—8 of FIG. 7 having a circular cross-section; and FIG. 9 is a sectional view of an alternative to the fingergrip of FIG. 8 having an elliptical cross-section.

DETAILED DESCRIPTION OF THE PREFERRED EMBODIMENTS

Figure 1:
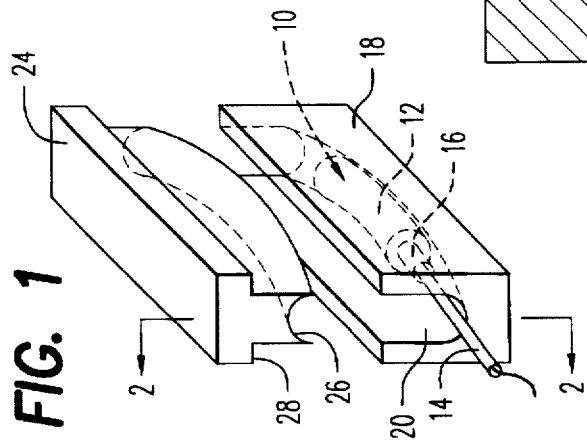
FIG. 1 is a perspective view of a two-part mold and curved tampon assembly formed therein in accordance with a first preferred embodiment of the present invention.

Referring to the drawings and, in particular, to FIG. 1, there is provided a tampon assembly which is generally represented by reference numeral 10. The tampon assembly 10 includes a pledget 11 (shown in dotted lines in FIG. 2) and an applicator that includes a barrel component and a plunger 14. The barrel component includes a barrel 12 and a fingergrip 16. The applicator is, preferably, made of plastic, such as polyethylene, or other thermoplastic type materials. There is also provided an apparatus for forming the tampon assembly 10, which apparatus includes a lower mold 18 and an upper mold 24.

The barrel 12 and the plunger 14 of the applicator and the pledget 11 are formed using existing manufacturing methods. For example, the applicator may be formed by molding or extrusion using existing tampon manufacturing equipment and known methods for forming straight-shaped tampon applicators. These manufacturing and assembly equipment and methods are not discussed in detail in this application since they are well known in the art and are not a critical part of the present invention.

After each component of the tampon assembly is formed and the entire tampon assembly 10 is assembled, the present invention is employed. It is to be understood that the process of the present invention lends itself to reconforming the axial orientation of one or more components of an entire tampon assembly 10 and may be used to change the axial orientation of the entire tampon assembly as well.

Figure 3:
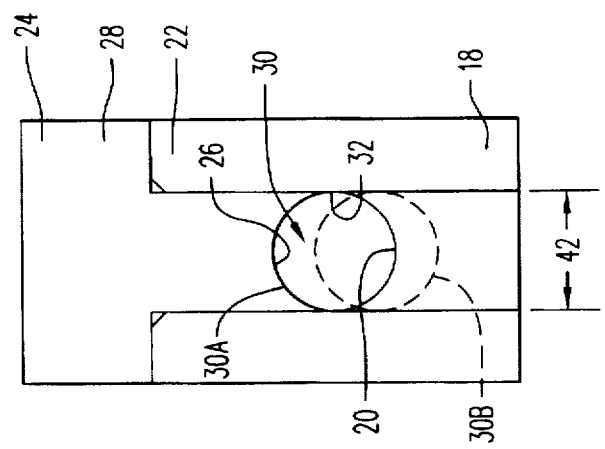
FIG. 3 is an end elevational view of the two-part mold of FIG. 2 with the upper and lower molds of the two-part mold joined together but with the curved tampon assembly not shown.
Figure 2:
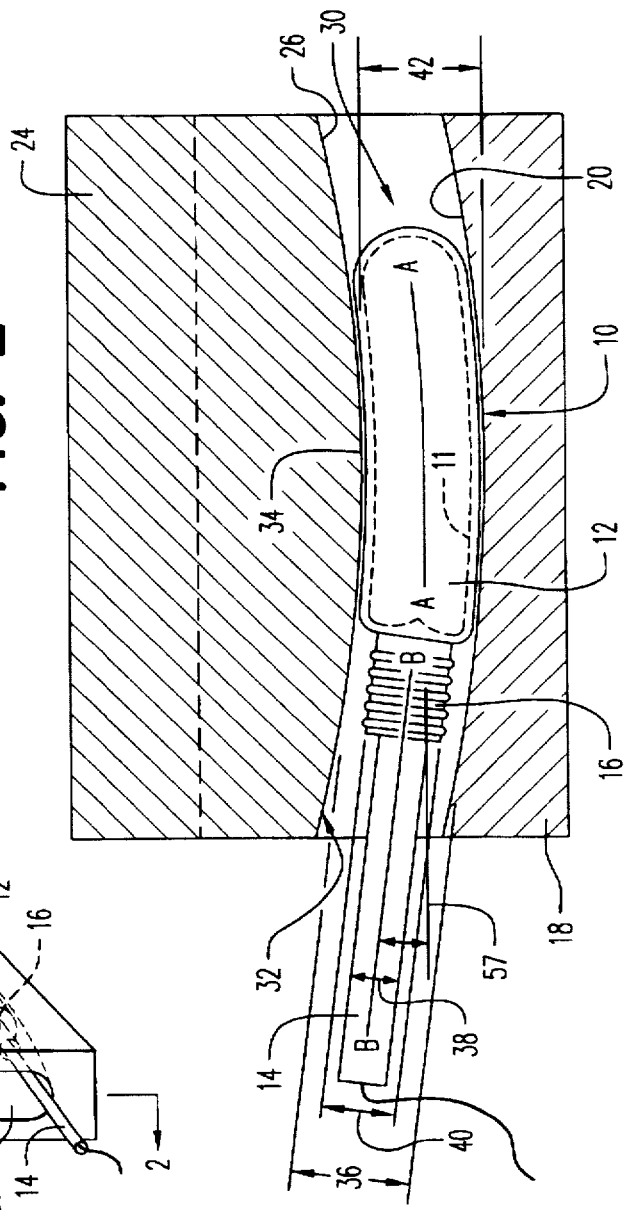
FIG. 2 is a cut-away view along line 2—2 of FIG. 1 with the upper and lower molds of the two-part mold joined together.

Referring to the first preferred embodiment shown in FIGS. 1 through 3, the barrel 12 will be post formed into a curved or arcuate axial orientation while the plunger 14 remains straight. The tampon assembly 10 or a portion thereof, such as the barrel 12, is first heated at a predetermined elevated temperature to permit flexing and reorientation of the central axis A—A of the tampon assembly. Any type of conventional process for elevating the temperature of the tampon assembly 10 may be used, such as exposure to a hot air oven or infrared heating, so long as the tampon assembly, and especially the pledget 11, is not harmed or otherwise rendered unusable. Infrared heating is preferred due to its ability to rapidly heat a tampon assembly 10 and direct its heat to desired portions of the tampon assembly. For instance, the predetermined heating range is about 150 degrees to about 250 degrees Fahrenheit for polyethylene.

By heating the barrel 12 of the tampon assembly 10, the structure of the barrel is softened so that it can be curved or otherwise shaped. This heating is preferably accomplished at a rapid rate so that the cycle time for heating the barrel 12 is minimized and excessive quantities of heat energy do not have to be withdrawn from the barrel to set the new axial orientation. To assure that heating is uniform, the tampon assembly 10 is rotated during heating. Preferably, the tampon assembly 10 is rotated at a rotational surface speed from about 5 to 15 feet per minute for about 10 to 60 seconds. Also, the cycle time and radiant heat level for heating the barrel 12 is adjusted so that the barrel is heated to a level just below where it will start to soften excessively or become misshaped.

Referring specifically to FIG. 1, the heated tampon assembly 10 should be transferred to a cooling die, such as the lower mold 18 and the upper mold 24, as rapidly as possible after heating to maintain the utmost efficiency of process. Preferably, the heated barrel 12 should be transferred into the cooling die within about two seconds. During the cooling process, the barrel 12 and the pledget 11 therein shall basically take the arcuate axial orientation. Thus, the initially straight formed tampon assembly 10, now having a heated barrel 12, is situated on a substantially cylindrical, curved inner surface 20 of the lower mold 18.

Referring to FIGS. 2 and 3, when the lower mold 18 and the upper mold 24 are joined, they form a mold cavity 30 that compresses the heated tampon assembly 10, and in particular the heated barrel 12. The mold cavity 30 has a longitudinal arcuate orientation, represented by centerline A—A, based on a predetermined radius of curvature 34. The level of compression subjected to the lower mold 18 and the upper mold 24 is sufficient to fully close the two-part mold.

The lower mold 18 and the upper mold 24 are joined together, as stated above, such that an upper shoulder 22 of the lower mold 18 abuts a lower flange or shoulder 28 of the upper mold 24. In this joined position, a surface 20 of the lower mold 18 and a surface 26 of the upper mold 24 form the mold cavity 30 therein. As shown in FIG. 2, the surfaces 20, 26 have an elongated, arcuate shape that complement each other to form a curved cylindrical hole in which the barrel 12 is curved into the desired shape. As noted in FIG. 2, the fingergrip 16 portion of the barrel 12 and the plunger 14 do not contact either the lower mold 18 or the upper mold 24 and therefore their original straight axial orientations and shapes are not affected by the molds.

The arcuate shapes of the surfaces 20, 26 are also represented in FIG. 3. In particular, the solid circle 30A formed by the surfaces 20, 26 shows the view of the mold cavity 30 from one end of the two-part mold, while the downwardly offset dashed circle 30B represents the middle cross-section of the mold cavity 30, which is the lowest position of the mold cavity within the two-part mold. Accordingly, the circles 30A and 30B represent the curvature of the barrel 12 and the pledget 11 therein.

The heated barrel 12 is compressed and held within the fully closed, non-heated mold cavity 30 until the tampon assembly reaches a predetermined reduced temperature. Although a cooling mechanism (not shown) for controlling the temperature of the lower mold 18 and/or the upper mold 24 is not necessary, such a mechanism may be used in order to expedite the cooling process or otherwise increase performance. For example, a cooling media may be circulated throughout the lower mold 18 and the upper mold 24 or the molds may be air cooled. Preferably, in order to sustain a preferred cooling time period of about 35 seconds, a coolant having a constant temperature about 65 degrees Fahrenheit is circulated through the lower mold 18 and the upper mold 24. For instance, the predetermined reduced temperature may range from about 90 degrees to about 150 degrees Fahrenheit for a polyethylene applicator.

Like the mold cavity 30, the barrel 12 shall have an arcuate shape that corresponds to centerline A—A while it is positioned within the mold cavity. However, in virtually every instance, the tampon assembly 10 does not take the exact form of the mold cavity 30 since certain materials, such as thermoplastics, have a memory and tend to counter-curve back slightly toward their original straight form upon removal from the mold cavity 30. In order to produce a tampon assembly 10 having a particular radius of curvature, the mold cavity 30 where it is formed must have a slightly smaller radius of curvature 34 to compensate for offset caused by the memory. The arcuate shape represented by centerline A—A has a radius of curvature 34 of about 3 inches to about 6 inches in order to form a final tampon assembly 10 having a radius of curvature of about 5 inches to about 11 inches. Preferably, the radius of curvature 34 of centerline A—A is about 4 inches and the radius of curvature of the final tampon assembly is about 10 inches.

A fingergrip 16 is located at one end of the barrel 12 adjacent the plunger 14. The fingergrip 16 and plunger 14 have a straight form, represented by centerline B—B. The plunger 14 has a diameter 38 that is less than a diameter 40 of the fingergrip 16 of the barrel 12. The diameters of the plunger 14 and fingergrip 16 are less than that of the barrel 12 and of such an extent that neither the plunger 14 nor the fingergrip 16 contact any inner surface of the mold cavity 30.

To remove the tampon assembly 10 from the molds, the lower mold 18 is separated from the upper mold 24. The tampon assembly 10 that has been post formed and removed from the lower and upper molds 18, 24, has a new axial orientation that is, preferably, curved. Since no further manufacturing or assembly of components is required, the tampon assembly 10 is ready for packaging and distribution.

In contrast to the first preferred embodiment, the configurations of the mold cavities for the other preferred embodiments, described below, are different than that of the first preferred embodiment. The specific mold cavities substantially affect the steps of positioning and holding of the tampon assembly 10. On the other hand, the steps of heating and removing of the tampon assembly 10 for the following embodiments are virtually identical to the corresponding steps of the first preferred embodiment, as described above. Therefore, only the aspects of positioning and holding of the tampon assembly 10 that differ from the first preferred embodiment are discussed below.

Referring to FIG. 4, there is shown a second preferred embodiment of the tampon assembly 10 and the two-part mold. For this second preferred embodiment, the upper mold 46 is, preferably, an L-shaped member having an upper or horizontal portion 47A and an integral vertical portion 47B. The vertical portion 47B includes an aperture 48 adjacent the mold cavity 50 for supporting the fingergrip 16 and, also, the plunger 14 of the tampon assembly 10. Due to aperture 48 in the upper mold, the lower mold 44 does not assist in curving the shape of the fingergrip 16 of the tampon assembly 10. This aperture serves to hold the fingergrip 16 at a particular angle 56 relative to the tangent line 57 to the centerline A—A of the tampon assembly 10 during the cooling step. As a result, the fingergrip 16 and plunger 14 of the tampon assembly 10 shall have greater angularity than that of the first preferred embodiment.

Referring to FIG. 5, the inner surfaces of the lower mold 44 and the upper mold 46 that form the mold cavity 50 are used to reshape the barrel 12 of the tampon assembly 10 and function similarly to the corresponding elements of the first preferred embodiment. Similar to the first preferred embodiment, the two-part mold of this second preferred embodiment does not affect the straight form of the plunger 14. However, one distinguishing feature of the second preferred embodiment is that the fingergrip 16 of the barrel 12 is supported solely by the aperture 48 of the upper mold 46 and introduces a greater angle with respect to the tangent line 57 of the centerline A—A than the first embodiment.

The outer surface of the fingergrip 16, preferably, has a plurality of protuberances or grips 52. The outside diameter 40 of the fingergrip 16, as measured at the protuberances 52, is greater than the outside diameter 58 of the remainder of the plunger 14 and is no smaller than, and preferably about the same as, the diameter 54 of the aperture 48. Since the diameter 40 of the fingergrip 16 is equal to or greater than the diameter 54 of the aperture 48, the aperture forms a well-supported fit or grip with the fingergrip 16 to bend or reshape the heated fingergrip.

This well-supported fit or grip of the fingergrip 16 by aperture 48 holds the tampon securely so that the fingergrip of the barrel 12 is bent at a particular angle 56 relative to the remainder of the barrel. In comparing FIGS. 2 and 6, it can be seen that centerline C—C of the plunger 14 and fingergrip 16 of the second preferred embodiment is bent at a greater angle with respect to the horizontal position than the center line B—B of these components in the first preferred embodiment.

Referring to FIG. 6, the diameter 54 of the aperture 48 of the upper mold 46 is shown relative to the diameter 42 of the mold cavity 50. The constricted or narrower size of the aperture 48 is necessary to grip or position of the fingergrip 16 by the upper mold 46, as described above.

Referring to FIG. 7, there is shown a third preferred embodiment of the two-part mold and tampon assembly of the present invention. The third preferred embodiment provides for post forming the entire tampon assembly 10, i.e. the barrel 12 with tampon pledget 11 and the plunger 14, into a curved tampon assembly. Thus, the entire tampon assembly 10 is post-formed into virtually a single predetermined radius of curvature 34. In particular, it is intended that the centerline of the barrel 12, the fingergrip 16 and the plunger 14 is the same so that a single radius of curvature 34 as shown by centerline D—D is achieved for the entire tampon assembly 10.

To achieve the simultaneous reshaping or bending of the entire tampon assembly 10, the upper and lower molds include three sections of mating inner surfaces 76, 78 & 80. Inner surfaces 76 form mold cavity 70 the tampon barrel 12, inner surfaces 78 form a cavity 72 for the fingergrip 16, while inner surfaces 80 form a cavity 74 for the plunger 14. In each instance, the inner surfaces 76, 78 & 80 contact the heated portion of the tampon assembly 10, namely the barrel 12, the fingergrip 16 and the plunger 14, to reshape or curve the axial orientation of that component.

In order to form the curved plunger 14 of the third preferred embodiment, the plunger is heated simultaneously with the barrel 12 before being positioned in the molds 64, 66. After positioning, the barrel 12 is compressed within the mold cavity 70, the plunger 14 is compressed within cavity 74 and the fingergrip 16 is compressed within cavity 72. These portions of the tampon assembly 10 are held within their respective cavities until the tampon assembly reaches the predetermined reduced temperature. Accordingly, when the tampon assembly 10 is removed, it will substantially correspond with the curved shape of the cavities 72, 74 defined by centerlines A—A and D—D.

To curve the axis of the plunger 14, cavity 74 must be long enough to enclose the entire plunger, as shown in FIG. 7. This is in contrast to the shorter mold construction of the first preferred embodiment where the plunger 14 extends out of one end of the two-part mold 18, 24, as shown in FIG. 2.

Referring to FIGS. 7 through 9, the cavity 74 for the plunger 14 and the cavity 72 for the fingergrip 16 form the cross-section of the plunger and the fingergrip into a predetermined geometric shape. The present invention is not limited to objects or devices having a circular cross-section. The post-forming process of the present invention performs well for objects or devices having a cross-section that is oval, square, or otherwise non-circular in shape. In FIG. 8, the cavity 72 for the fingergrip 16 encloses the fingergrip, as well as a portion of the plunger 14 that is situated in the fingergrip, to form a circular, cross-sectional shape for the fingergrip and a similar circular, cross-sectional shape for the plunger. The present invention provides a method to form a wide variety of different geometric shapes for the fingergrip 16 and the plunger 14 of the tampon assembly 10. By example, the fingergrip 16 and the plunger 14 may have an elliptical, cross-sectional shape as shown in FIG. 9.

The lower molds 18, 44 & 64 and upper molds 24, 46 & 66 of each embodiment of the present invention may be made of any type of material or materials that may handle the tampon assembly 10 after the heating process described above. In particular, the material must be capable of being machined to a desired shape and conducting heat away from the tampon assembly 10 at a rapid rate. In addition, each mold cavity of each embodiment must be capable of compressing the desired portions of the tampon assembly 10 as described above during the compressing process. The acceptable materials include, but are not limited to, metallic materials, and preferably aluminum.

The barrel 12 including the integral fingergrip 16 and the plunger 14 of the tampon assembly 10 may be made of any type of material or materials that may be injection molded or extruded. The materials must be heat resistant to the elevated temperatures of the heating process and tension resistant to the pressure levels of the compressing process, which processes have been described above. The materials include, but are not limited to, thermoplastics.

The pledget 11 may be made of any type of soft material that curves naturally within the barrel 12 during the methods of the present invention. These materials include, but are not limited to, cotton, cotton/rayon blends, and rayon. Also, it has been determined that, in addition to utilizing a soft material, lengthening and thinning the dimensions of the pledget 11 permits it to move freely within the barrel. This free movement facilitates formation of its curved shape during the compression of the barrel in the two-part mold and ejection of the pledget 11 from the barrel.

In summary, the post forming steps, i.e., steps executed after assembly of the components of the tampon assembly 10, provide an efficient and economical method of producing a curved tampon assembly. The method, which includes heating, positioning, holding during cool-down and removing the tampon assembly 10, causes a second or reorientation of the tampon assembly into a new axial orientation, preferably called a curved shape, without the need to purchase or otherwise obtain manufacturing and assembling equipment that are specially designed to handle curved components.

While this application presents a first preferred embodiment shown in FIGS. 1 through 3, a second preferred embodiment shown in FIGS. 4 through 6, and a third preferred embodiment shown in FIGS. 7 through 9, other possible combinations not explicitly shown can be derived based on these embodiments.

It is to be understood that the post-forming or axial reorientation process of the present invention is not intended to be limited to tampon assemblies. It is contemplated that the above described process may be used to reconfigure a wide variety of objects or devices that may desire a new shape, particularly a curved shape.

The present invention having been thus described with particular reference to the preferred forms thereof, it will be obvious that various changes and modifications may be made therein without departing from the spirit and scope of the invention as defined in the appended claims.

Wherefore, we claim:

1. A method for post forming a portion of a formed tampon assembly into a curved axial orientation, said formed tampon assembly including a barrel having a pledget therein and a plunger connected to the barrel, the method comprising the steps of:

heating said portion of said formed tampon assembly to a predetermined elevated temperature to permit flexing and reorienting of said portion;

positioning said portion of said formed tampon assembly in a mold cavity having a longitudinal arcuate orientation based on a predetermined radius of curvature, said positioning causing said portion of said formed tampon assembly to adapt initially to the arcuate orientation of said mold cavity;

holding said portion of said formed tampon assembly in said mold cavity until said portion cools to a predetermined reduced temperature; and removing said portion from said mold cavity, wherein the removed portion has the curved axial orientation.

2. The method for post forming of claim 1, wherein said portion of said formed tampon assembly comprises at least one tampon assembly component selected from the group consisting of: a barrel of a barrel component, a fingergrip of a barrel component and a plunger.

3. The method for post forming of claim 1, wherein the step of positioning said portion of said formed tampon assembly in said mold cavity includes compressing said portion between an upper mold and a lower mold, wherein said upper mold and said lower mold form said longitudinal arcuate orientation of said mold cavity when said portion is fully compressed therebetween.

4. The method for post forming of claim 3, wherein the step of positioning said portion of said formed tampon assembly in said mold cavity includes situating said formed tampon assembly on said lower mold before compressing said portion between said upper mold and said lower mold.

5. The method for post forming of claim 3, wherein the step of positioning said portion of said formed tampon assembly in said mold cavity includes situating said formed tampon assembly on said upper mold before compressing said portion between said upper mold and said lower mold.

6. The method for post forming of claim 3, wherein the step of positioning said portion of said formed tampon assembly in said mold cavity includes gripping a fingergrip of said barrel of said formed tampon assembly, before compressing said portion, to provide greater angularity between said fingergrip and a remainder of said barrel of said formed tampon assembly.

7. The method for post forming of claim 6, wherein the step of gripping said fingergrip of said formed tampon assembly includes gripping at least one protrusion formed on an outer surface of said fingergrip to facilitate gripping thereof.

8. The method for post forming of claim 6, wherein the step of gripping said fingergrip of said formed tampon assembly includes bending said fingergrip at a particular angle relative to the remainder of said barrel of said formed tampon assembly.

9. The method for post forming of claim 1, wherein the step of positioning said portion of said formed tampon assembly in said mold cavity includes compressing a fingergrip of said barrel of said formed tampon assembly between an upper mold and a lower mold, wherein a cross-section of said fingergrip is formed into a predetermined shape.

10. The method of post forming of claim 1, wherein the step of positioning said portion of said formed tampon assembly in said mold cavity includes positioning an end portion of said plunger of said formed tampon assembly in a fingergrip of said barrel of said formed tampon assembly and compressing said plunger and said fingergrip between an upper mold and a lower mold, wherein cross-sections of said plunger and said fingergrip are formed into similar predetermined shapes.

11. The method for post forming of claim 1, further comprising a step of packaging said formed tampon assembly, directly after removing said formed tampon assembly from said mold cavity.

12. The method for post forming of claim 1, wherein said predetermined elevated temperature is about 150 degrees to about 250 degrees Fahrenheit.

13. The method for post forming of claim 1, wherein said predetermined reduced temperature is about 90 degrees to about 150 degrees Fahrenheit.

14. The method for post forming of claim 1, wherein said predetermined radius of curvature of said longitudinal arcuate orientation is about 3 inches to about 6 inches.

15. The method for post forming of claim 1, wherein said curved axial orientation of the removed portion has a desired radius of curvature of about 5 inches to about 11 inches.

16. A method for post forming a formed tampon assembly into a curved tampon assembly, said formed tampon assembly including a barrel with a pledget therein and a plunger connected to the barrel, the method comprising the steps of:

heating said formed tampon assembly to a predetermined elevated temperature to permit flexing and reorienting of said formed tampon assembly;

positioning said formed tampon assembly in a mold cavity having a longitudinal arcuate orientation based on a predetermined radius of curvature, said positioning causing said formed tampon assembly to adapt initially to the arcuate orientation of said mold cavity;

holding said formed tampon assembly in said mold cavity until said formed tampon assembly cools to a predetermined reduced temperature; and removing said formed tampon assembly from said mold cavity, wherein the removed, formed tampon assembly has a curved axial orientation.

17. The method for post forming of claim 16, wherein said tampon assembly comprises a barrel, a fingergrip and a plunger.

18. The method for post forming of claim 16, wherein the step of positioning said formed tampon assembly in said mold cavity includes compressing said formed tampon assembly between an upper mold and a lower mold, wherein said upper mold and said lower mold form said longitudinal arcuate orientation of said mold cavity when said formed tampon assembly is fully compressed therebetween.

19. The method for post forming of claim 16, wherein the step of positioning said formed tampon assembly in said mold cavity includes compressing a fingergrip of said barrel of said formed tampon assembly between an upper mold and a lower mold, wherein a cross-section of said fingergrip is formed into a predetermined shape.

20. The method of post forming of claim 16, wherein the step of positioning said formed tampon assembly in said mold cavity includes positioning an end portion of said plunger of said formed tampon assembly in said fingergrip of said barrel of said formed tampon assembly and compressing said plunger and said fingergrip between an upper mold and a lower mold, wherein cross-sections of said plunger and said fingergrip are formed into similar predetermined shapes.

21. The method for post forming of claim 16, further comprising a step of packaging said formed tampon assembly, directly after removing said formed tampon assembly from said mold cavity.

22. The method for post forming of claim 16, wherein said predetermined elevated temperature is about 150 degrees to about 250 degrees Fahrenheit.

23. The method for post forming of claim 16, wherein said predetermined reduced temperature is about 90 degrees to about 150 degrees Fahrenheit.

24. The method for post forming of claim 16, wherein said predetermined radius of curvature of said longitudinal arcuate orientation is about 3 inches to about 6 inches.

25. The method for post forming of claim 16, wherein said curved axial orientation of the removed portion has a desired radius of curvature of about 5 inches to about 11 inches.

* * * * *